United States Patent
Dawley et al.

(10) Patent No.: US 10,114,062 B2
(45) Date of Patent: Oct. 30, 2018

(54) METHOD AND APARATUS FOR MONITORING A JUNCTION BETWEEN ELECTRICAL DEVICES

(71) Applicant: GM GLOBAL TECHNOLOGY OPERATIONS LLC, Detroit, MI (US)

(72) Inventors: Evan J. Dawley, Lake Orion, MI (US); Edgar P. Calderon, Sterling Heights, MI (US); Cammi L. Siu, Macomb, MI (US); Lance W. Turner, Macomb, MI (US)

(73) Assignee: GM Global Technology Operations LLC, Detroit, MI (US)

( * ) Notice: Subject to any disclaimer, the term of this patent is extended or adjusted under 35 U.S.C. 154(b) by 210 days.

(21) Appl. No.: 15/266,213

(22) Filed: Sep. 15, 2016

(65) Prior Publication Data
US 2017/0322251 A1    Nov. 9, 2017

Related U.S. Application Data

(60) Provisional application No. 62/331,659, filed on May 4, 2016.

(51) Int. Cl.
*G01R 31/00* (2006.01)
*G01R 31/04* (2006.01)
(Continued)

(52) U.S. Cl.
CPC ............. *G01R 31/046* (2013.01); *G01N 3/34* (2013.01); *G01N 3/36* (2013.01); *G01R 31/3644* (2013.01);
(Continued)

(58) Field of Classification Search
CPC ........ G01R 31/40; G01R 31/42; G01R 31/26; G01R 31/2642; G01R 31/2648;
(Continued)

(56) References Cited

U.S. PATENT DOCUMENTS

| 5,218,303 A | * | 6/1993 | Medvinsky | .......... G01N 27/416 205/790 |
| 2002/0076689 A1 | * | 6/2002 | Farb | .................. G01N 33/48728 435/4 |

FOREIGN PATENT DOCUMENTS

| DE | 2441690 A1 | 3/1976 |
| DE | 125175 A1 | 4/1977 |

(Continued)

*Primary Examiner* — Tung X Nguyen
(74) *Attorney, Agent, or Firm* — Quinn IP Law

(57) ABSTRACT

A method and a test fixture for evaluating a junction between an electrical lead trace and a busbar are described, and include an electric power supply disposed to supply electric power to the electrical lead trace and an electric monitoring device disposed to monitor electrical potential across the junction. A mechanical stress-inducing device is disposed to apply mechanical stress proximal to the junction. The electric monitoring device monitors the electrical potential across the junction of the electrical lead trace coincident with the mechanical stress-inducing device applying mechanical stress proximal to the junction when the electric power supply is supplying electric power to the electrical lead trace. Electrical integrity of the junction is evaluated based upon the monitored electrical potential across the junction.

20 Claims, 3 Drawing Sheets

(51) Int. Cl.
*G01N 3/34* (2006.01)
*G01N 3/36* (2006.01)
*G01R 31/36* (2006.01)
*G01N 3/30* (2006.01)

(52) U.S. Cl.
CPC ....... *G01N 3/30* (2013.01); *G01N 2203/0039* (2013.01); *G01N 2203/0617* (2013.01)

(58) Field of Classification Search
CPC .......... G01R 31/2831; G01R 31/31702; G01R 31/3658; G01N 31/02; G01N 27/42
See application file for complete search history.

(56) References Cited

FOREIGN PATENT DOCUMENTS

| | | |
|---|---|---|
| DE | 3905856 C1 | 5/1990 |
| DE | 102007032560 A1 | 1/2009 |

\* cited by examiner

METHOD AND APARATUS FOR MONITORING A JUNCTION BETWEEN ELECTRICAL DEVICES

CROSS-REFERENCE TO RELATED APPLICATIONS

This application claims the benefit of U.S. Provisional Patent Application No. 62/331,659 filed on May 4, 2016, the disclosure of which is hereby incorporated by reference.

TECHNICAL FIELD

This disclosure relates to junctions between electrical devices, and monitoring thereof.

BACKGROUND

A battery pack typically includes multiple rechargeable battery cells that are connected in series or parallel to store and supply electric power to a distribution system. Terminals of adjacent battery cells are joined at busbars, and electrical lead traces may electrically connect to the busbars for monitoring purposes. Joining of electrical lead traces to busbars may be accomplished employing a mechanical fastener, e.g., a rivet. There are opportunities for improvement of methods and test fixtures to evaluate electrical integrity of such a mechanical fastener at assembly. Known methods for evaluating electrical integrity include static impedance tests and visual inspections.

SUMMARY

A method and a test fixture for evaluating a junction between an electrical lead trace and a busbar are described, and include an electric power supply disposed to supply electric power to the electrical lead trace and an electric monitoring device disposed to monitor electrical potential across the junction. A mechanical stress-inducing device is disposed to apply mechanical stress proximal to the junction. The electric monitoring device monitors the electrical potential across the junction of the electrical lead trace coincident with the mechanical stress-inducing device applying mechanical stress proximal to the junction when the electric power supply is supplying electric power to the electrical lead trace. Electrical integrity of the junction is evaluated based upon the monitored electrical potential across the junction.

The above features and advantages, and other features and advantages, of the present teachings are readily apparent from the following detailed description of some of the best modes and other embodiments for carrying out the present teachings, as defined in the appended claims, when taken in connection with the accompanying drawings.

BRIEF DESCRIPTION OF THE DRAWINGS

One or more embodiments will now be described, by way of example, with reference to the accompanying drawings, in which:

FIGS. 3-1 and 3-2 graphically show results associated with employing the test fixture described with reference to FIG. 2 to evaluate one of the electrical lead traces described with reference to FIG. 1, in accordance with the disclosure.

DETAILED DESCRIPTION

Figure 1:
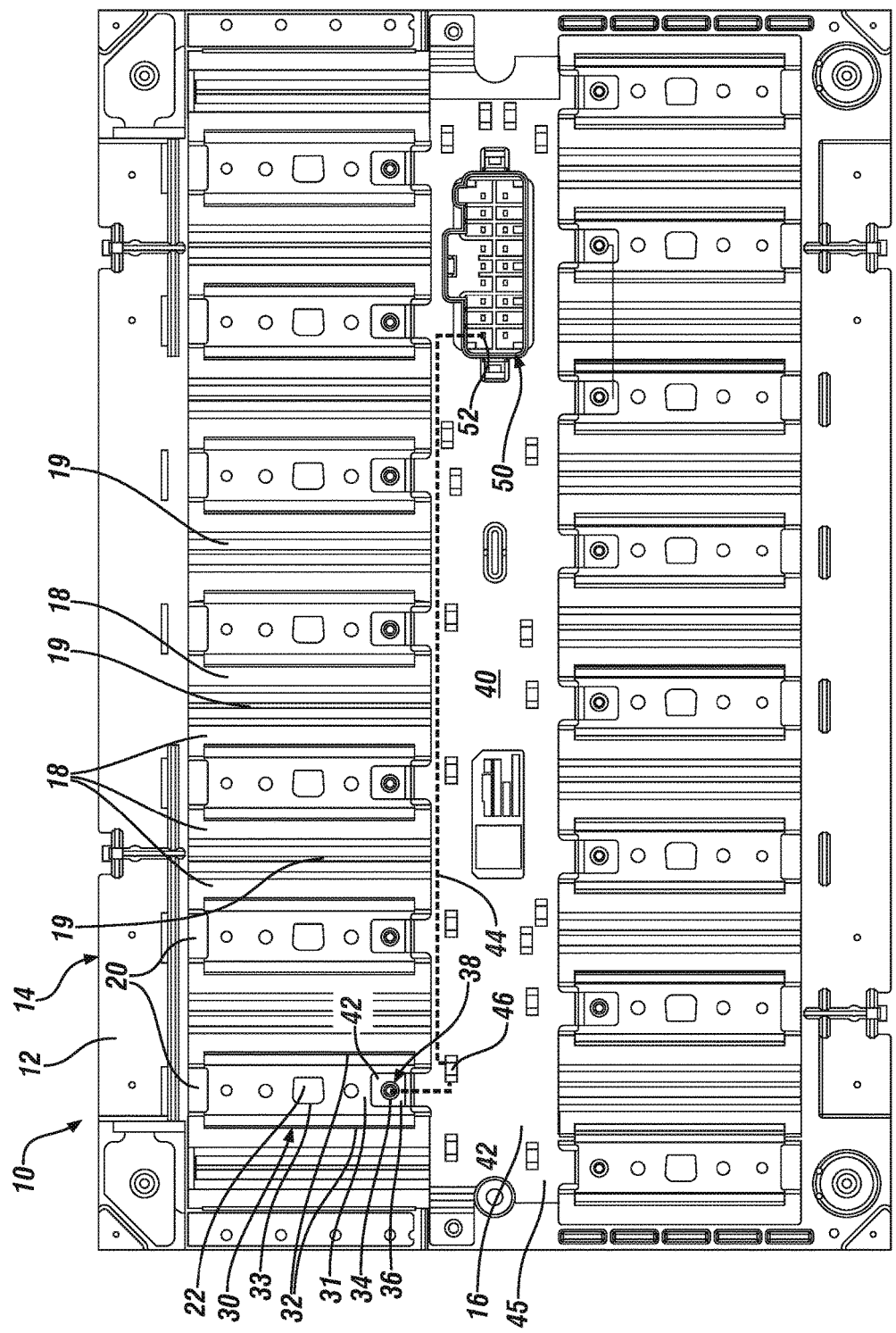
FIG. 1 is a schematic top plan view of a battery cell interconnect board including a plurality of electrically conductive busbars disposed in a frame, in accordance with the disclosure.

Referring now to the drawings, which are provided for the purpose of illustrating certain exemplary embodiments only and not for the purpose of limiting the same, FIG. 1 schematically illustrates a battery cell interconnect board 10 including a plurality of electrically conductive busbars 30 that are disposed in a non-conductive frame 12, and an accompanying monitoring circuit 40 that includes an electrical connector 50. The battery cell interconnect board 10 is advantageously disposed on a second frame portion (not shown) that houses a plurality of rechargeable battery cells (not shown). The battery cell interconnect board 10 and the second frame portion together form a battery pack. The battery cells each have a positive terminal and a negative terminal, and subsets of the positive or negative terminals are welded to one of the busbars 30. The battery cells may be connected in series or parallel through the battery cell interconnect board 10 to store and supply electric power to an electric power distribution system. The battery pack may be disposed on a vehicle in one embodiment to supply electric power to propulsion systems and other systems, depending upon the specific application. Those having ordinary skill in the art will recognize that terms such as "horizontal", "vertical", "above," "below," "upward," "downward," "top," "bottom," etc., are used descriptively for the figures, and do not represent limitations on the scope of the disclosure, as defined by the appended claims. Furthermore, the disclosure, as illustrated and described herein, may be practiced in the absence of any element which is not specifically disclosed herein.

Each busbar 30 is fabricated from conductive material, e.g., copper, and preferably includes a web portion 31 and side portions 32, with a first aperture 33 and a second aperture 34 formed in the web portion 31. The first aperture 33 is preferably centrally disposed on the web portion 31 along its longitudinal axis, and the second aperture 34 is preferably disposed near one of the ends of the web portion 31. Subsets of the positive or negative terminals of the battery cell are welded to side portions 32 of the busbars 30.

The battery cell interconnect board 10 includes the electrically conductive busbars 30 disposed in the non-conductive frame 12. The frame 12 may be a rectangularly-shaped rigid device that is fabricated from non-conductive thermoplastic material, e.g., polycarbonate, using injection molding or another suitable process. The frame 12 includes an outer peripheral portion 14, a central bridge 16, a plurality of reinforcement ribs 19 and a plurality of side bridges 20. A plurality of apertures 18 are formed between adjacent reinforcement ribs 19 and side bridges 20. The apertures 18 accommodate either the positive terminals or the negative terminals from a subset of the battery cells, which extend therethrough to permit welding to the side portions 32 of one of the busbars 30 during a subsequent assembly process. In one embodiment, the battery cell interconnect board 10 is formed by overmolding the frame 12 onto the plurality of busbars 30, wherein each of the busbars 30 is oriented with the second aperture 34 proximal to the central bridge 16. Each of the busbars 30 preferably includes protrusion portions that secure the busbars 30 into the frame 12 as part of the overmolding process. Alternatively, the frame 12 molded such that each of the side bridges 20 includes a protrusion portion 22 that extends upwardly from the surface of the side bridge 20. The busbars 30 are assembled onto the side bridges 20 such that the web portion 31 of each busbar 30 is contiguous with the side bridge 20. Each busbar 30 is oriented to have its second aperture 34 proximal to the central bridge 16, and the protrusion portion 22 of the side bridge 20 is inserted into the first aperture 33. Heat is then applied to plastically deform the protrusion portion 22 and fixedly secure the busbar 30 to the side bridge 20.

The monitoring circuit 40 includes a plurality of electrical lead traces 44 that are fabricated onto a non-conductive flexible web material 45, wherein the electrical lead traces 44 electrically connect between the busbars 30 and terminal pins 52 of the connector 50 for monitoring and signal communication. One of the electrical lead traces 44 electrically connects between one of the busbars 30 and one of the terminal pins 52 of the connector 50, and preferably includes an in-series fuse 46. A single electrical lead trace 44, fuse 46 and terminal pin 52 are shown for ease of illustration. In use, the connector 50 communicates electrical information gathered from the subsets of the battery cells via the busbars 30 for purposes of monitoring, load balancing, fault detection, etc. The electrical connector 50 includes a plurality of terminal pins 52 that are arranged in a structured body to effect connection to another device, such as a monitoring controller.

A portion of each electrical lead trace 44 and a portion of the web material 45 is formed into a tab 42 that preferably overlaps with one of the busbars 30 such that the tab 42 is adjacent with the second aperture 34 of the web portion 31 of the busbar 30. The tab 42 is fixedly secured to the busbar 30 employing a permanent mechanical fastener 36, such as a rivet, which forms a junction 38 between the tab 42 and the busbar 30. Each mechanical fastener 36 forms the junction 38 by applying a normal force that compresses adjoining surfaces of the busbar 30 and the portion of the electrical lead trace 44 formed into the tab 42. The normal force may be applied by deforming a portion of the mechanical fastener 36 in one embodiment. Each junction 38 has two components, including a mechanical joining of the tab 42 and the busbar 30, and an electrically-conductive joining of the portion of the electrical lead trace 44 and the busbar 30. Mechanical fasteners 36 such as rivets are known.

Assembly processes associated with mechanically coupling a plurality of the tabs 42 to corresponding busbars 30 employing a plurality of mechanical fasteners 36 may be subject to variation. Such variation may be associated with the magnitude of the applied normal force due to the deformation of the mechanical fastener 36 during fabrication, wherein the variation may be non-obvious. Furthermore, one of the junctions 38 formed between one of the tabs 42 and one of the busbars 30 may appear to be mechanically sound but have a non-obvious difference that introduces variation in the electrical conductivity across the junction 38. This variation in the electrical conductivity may be immediately discernible, may be discernible after time and use, or may be discernible in response to an induced stress.

Each of the electrical lead traces 44 has a characteristic resistance that is determined based upon the trace length and pattern on the flexible web material 45, the fuse 46, solder and/or other interfaces, the terminal pin 52 and the junction 38 formed between the tab 42 and the busbar 30 by the mechanical fastener 36. The characteristic resistance may vary due to variation resistance at the junction 38, which may depend upon the magnitude of normal force that is applied by the mechanical fastener 36 to form the junction 38. By way of a non-limiting example, if a rivet is not formed properly during assembly, the rivet may have low clamping force, which may increase resistance at the junction 38.

Figure 2:
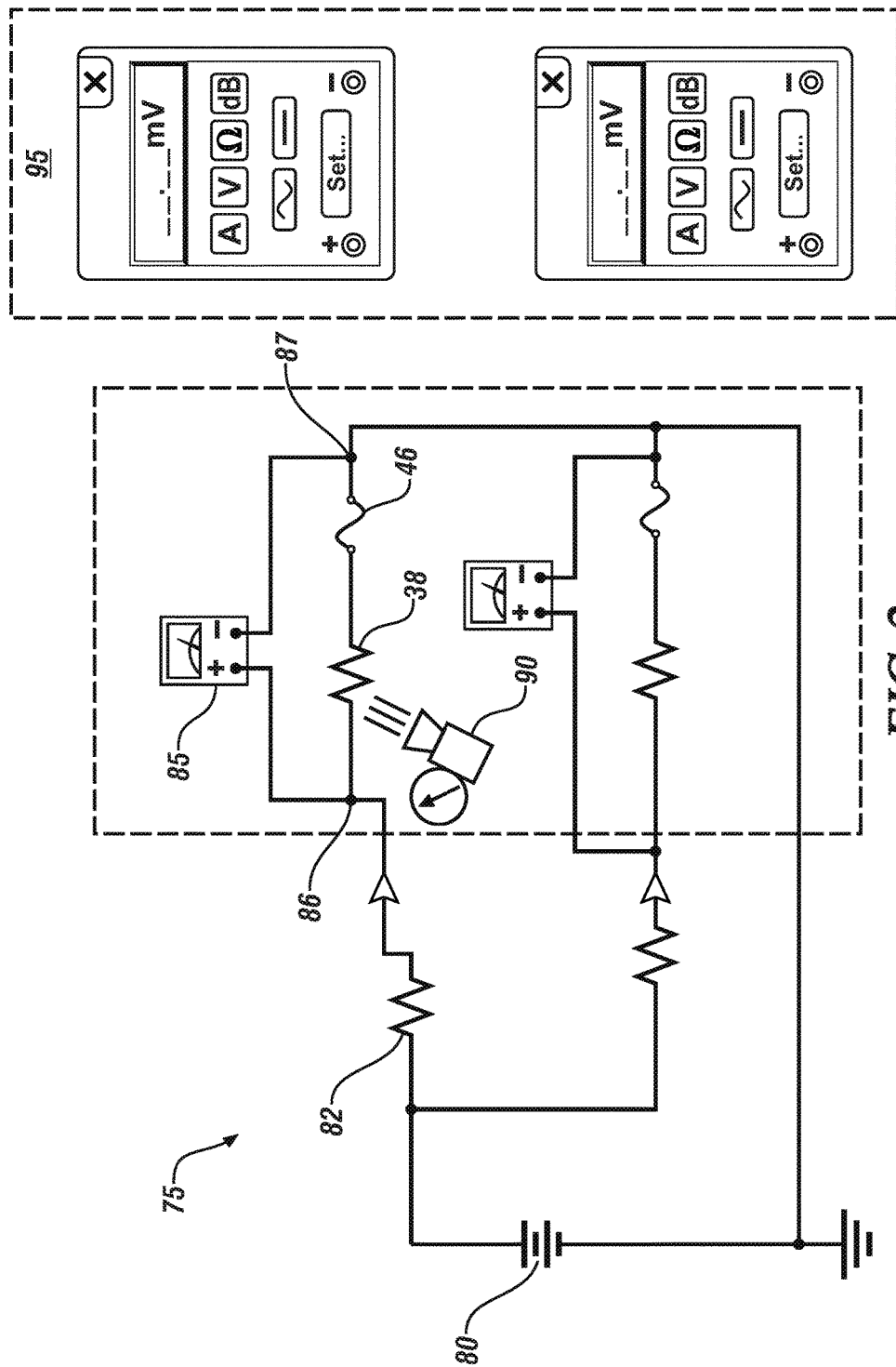
FIG. 2 schematically shows a test fixture associated with evaluating one of the electrical lead traces described with reference to FIG. 1, including an electric power supply, an electric monitoring device, a mechanical stress-inducing device and a controller in accordance with the disclosure.

FIG. 2 schematically shows a test fixture 75 associated with evaluating one of the electrical lead traces 44, and more specifically evaluating the electrical conductivity of one of the junctions 38 formed between the busbar 30 and the electrical lead trace 44 by the mechanical fastener 36. The junction 38 and an accompanying in-line fuse 46 are evaluated as resistive devices. The test fixture 75 is preferably configured to non-destructively evaluate the junction 38 formed between the busbar 30 and the electrical lead trace 44 by the mechanical fastener 36 on a workpiece. The test fixture 75 includes an electric power supply 80, an electric monitoring device 85, a mechanical stress-inducing device 90, and an associated controller 95. Overall, the controller 95 employs the test fixture 75 to measure a dynamic change in resistance at the junction 38 while the mechanical fastener 36 is subjected to an external non-destructive mechanical stress.

The electric power supply 80 is preferably a low-power device that electrically connects to a workpiece in the form of one of the electrical lead traces 44 to supply electric power at a preset voltage level. A load resistor 82 is placed in series with the electrical lead trace 44 to limit the current. The load resistor 82 is preferably selected to facilitate detecting a change in the monitored voltage that may occur due to a change in the overall resistance of the electrical lead trace 44, wherein the change in the monitored voltage may be caused by a change in the resistance across the junction 38. In one non-limiting embodiment, the preset voltage level is 0.5 volts DC.

The electric monitoring device 85 may be a voltmeter that is incorporated into a digital data acquisition device that monitors voltage, e.g., at a 1 kHz rate. The electric monitoring device 85 is preferably disposed to monitor a voltage between leads 86 and 87, which thus provides a voltage drop across the junction 38 and the in-line fuse 46. Connection to the lead 86 may be made via a pogo pin, and connection to the lead 87 may be made via the corresponding terminal pin 52 in the electrical connector 50.

The mechanical stress-inducing device 90 may be a device that is configured to apply mechanical stress proximal to the junction 38. The magnitude of the mechanical stress is sufficient to induce a discernible change in electrical resistance across the junction 38 when the junction 38 was not formed in accordance with specification, but limited so as to not induce new stress in the junction 38. The mechanical stress may be in the form of a burst of pressurized airflow that is applied to the junction 38, e.g., from a high-pressure source via a nozzle that is aimed towards the junction 38. Alternatively, the mechanical stress may be in the form of a direct mechanical tapping onto the junction 38, e.g., from a hammer device that is disposed to tap on the junction 38. Alternatively, the mechanical stress may be in the form of an induced vibration at the junction 38, e.g., from a horn of an ultrasonic welding device that is placed in contact with the junction 38. Alternatively, the mechanical stress may be in the form of another suitable mechanical stress.

The test fixture 75 preferably includes a controller 95 that executes one or more control routines to evaluate the integrity of the corresponding junction based upon the monitored electrical conductivity when applying the mechanical stress, which may be described as follows. In operation, one of the electrical lead traces 44 is secured and electrically connected to the electric power supply 80 and the electric monitoring device 85 of the test fixture 75. The mechanical stress-inducing device 90 is activated and the electric monitoring device 85 monitors voltage across the junction 38. The monitored voltage is evaluated. When there is a change in the monitored voltage associated with the induced stress, it may be indicative of an increased resistance in the junction 38 caused when the junction 38 was not formed in accordance with specification.

By way of a non-limiting example, a resistance level associated with an embodiment of the junction 38 that was formed in accordance with the specification may be in the order of magnitude of 2 milli-ohms, and a resistance level associated with an embodiment of the junction 38 that was not formed in accordance with the specification may be in the order of magnitude of 50 milli-ohms when mechanical stress is induced. As such, the electric monitoring device 85 must be configured to detect and discern between such levels. Preferably, there is a threshold voltage level, with minor changes in the increased resistance in the junction 38 not causing rejection of a workpiece. When there is no change in the monitored voltage associated with the induced stress, it may indicate that the junction 38 was formed in accordance with the specification.

Figures 1, 3:
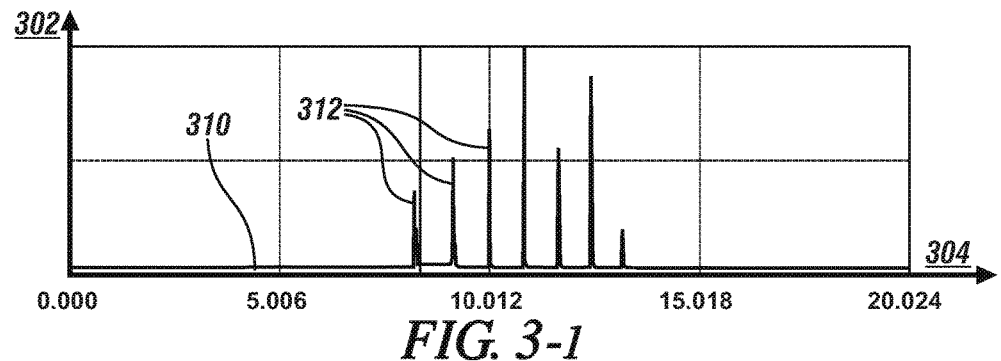
Figures 2, 3:
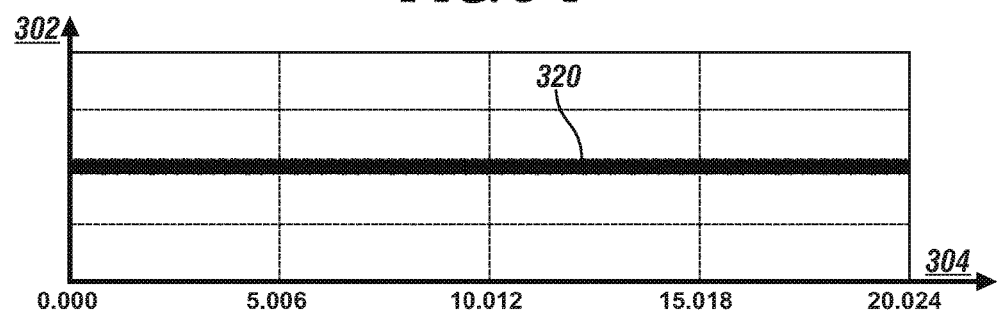

FIGS. 3-1 and 3-2 graphically show results associated with employing the test fixture 75 described with reference to FIG. 2 to evaluate one of the electrical lead traces 44 described with reference to FIG. 1. Voltage levels indicated by the electric monitoring device 85 are shown on the vertical scale 302, in relation to time, which is shown on the horizontal scale 304. The embodiment of the mechanical stress-inducing device 90 is in the form of a burst of pressurized airflow that is applied to the junction 38. The voltage spikes 310 shown in FIG. 3-1 include a plurality of voltage spikes 312, which are associated with repeated operation of an embodiment of the mechanical stress-inducing device 90 described with reference to FIG. 2, wherein the spikes 312 may indicate an increased resistance in the junction 38 caused when the junction 38 was not formed in accordance with specification. The voltage levels 320 shown in FIG. 3-2 do not include any voltage spikes that are associated with repeated operation of an embodiment of the mechanical stress-inducing device 90 described with reference to FIG. 2. This may indicate no increased resistance in the junction 38, i.e., the junction 38 was formed in accordance with specification and the workpiece may be deemed acceptable.

The terms controller, control module, module, control, control unit, processor and similar terms refer to any one or various combinations of Application Specific Integrated Circuit(s) (ASIC), electronic circuit(s), central processing unit(s), e.g., microprocessor(s) and associated non-transitory memory component in the form of memory and storage devices (read only, programmable read only, random access, hard drive, etc.). The non-transitory memory component is capable of storing machine readable instructions in the form of one or more software or firmware programs or routines, combinational logic circuit(s), input/output circuit(s) and devices, signal conditioning and buffer circuitry and other components that can be accessed by one or more processors to provide a described functionality. Input/output circuit(s) and devices include analog/digital converters and related devices that monitor inputs from sensors, with such inputs monitored at a preset sampling frequency or in response to a triggering event. Software, firmware, programs, instructions, control routines, code, algorithms and similar terms mean any controller-executable instruction sets including calibrations and look-up tables. Each controller executes control routine(s) to provide desired functions, including monitoring inputs from sensing devices and other networked controllers and executing control and diagnostic instructions to control operation of actuators. Routines may be executed at regular intervals, for example each 100 microseconds during ongoing operation. Alternatively, routines may be executed in response to occurrence of a triggering event. Communication between controllers, and communication between controllers, actuators and/or sensors may be accomplished using a direct wired point-to-point link, a networked communication bus link, a wireless link or any other suitable communication link. Communication includes exchanging data signals in any suitable form, including, for example, electrical signals via a conductive medium, electromagnetic signals via air, optical signals via optical waveguides, and the like. The data signals may include discrete, analog or digitized analog signals representing inputs from sensors, actuator commands, and communication between controllers. The term "signal" refers to any physically discernible indicator that conveys information, and may be any suitable waveform (e.g., electrical, optical, magnetic, mechanical or electromagnetic), such as DC, AC, sinusoidal-wave, triangular-wave, square-wave, vibration, and the like, that is capable of traveling through a medium.

Figure 4:
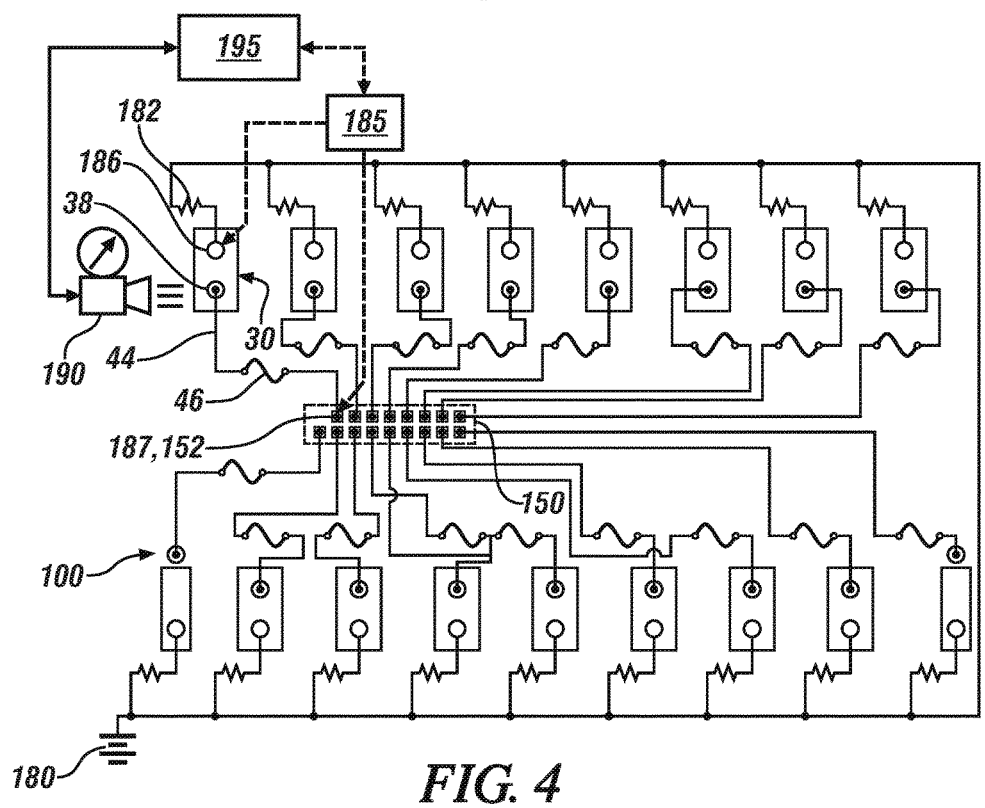
FIG. 4 schematically shows a plan view of an electrical circuit for an integrated test fixture and selected elements of the battery cell interconnect board that is described with reference to FIG. 1, in accordance with the disclosure.

FIG. 4 schematically shows a plan view of an electrical circuit for an integrated test fixture 100 and selected elements of the battery cell interconnect board 10 that are described with reference to FIG. 1. The integrated test fixture 100 includes elements of the test fixture 75 described with reference to FIG. 2, and is configured to monitor and evaluate a plurality of junctions 38 formed between corresponding tabs 42 and corresponding busbars 30 of the battery cell interconnect board 10. The integrated test fixture 100 includes an electric power supply 180, a plurality of electric monitoring devices 185, a mechanical stress-inducing device 190, an associated controller 195, and a plurality of load resistors 182 that may be placed in series with individual electrical lead traces 44 of the battery cell interconnect board 10. A single load resistor 182 is indicated in series with a single junction 38, electrical lead trace 44, and fuse 46 of the battery cell interconnect board 10, and is monitored via leads 186 and 187.

Each of the electrical lead traces 44 has a distinct characteristic resistance that is determined based upon the length, width and thickness of the electrical lead trace 44, its pattern on the flexible web material 45, the fuse 46, solder and/or other interfaces, the terminal pin 52 and the junction 38 formed between the tab 42 and the busbar 30 by the mechanical fastener 36. As such, the characteristic resistance may differ between individual ones of the electrical lead traces 44 in the battery cell interconnect board 10. As such each of the load resistors 182 is preferably selected to limit current draw such that all the electrical lead traces 44 of the battery cell interconnect board 10 have approximately the same current draw when all of the junctions 38 have been fabricated in accordance with the specification. As such, the voltage changes measured across the plurality of junctions 38 of the plurality of the electrical lead traces 44 will be equivalent. This configuration facilitates employing a single voltage threshold for monitoring all of the electrical lead traces 44 to detect whether the junctions 38 function in accordance with specification. This facilitates detecting a change in the monitored voltage that may occur due to a change in the overall resistance of the electrical lead trace 44, wherein the change in the monitored voltage may be caused by a change in the resistance across the junction 38. The monitored leads 186 and 187 are monitored via a voltmeter 185, which measures the voltage drop across the junction 38. The voltmeter 185 may be a stand-alone device that communicates with the controller 195, or may be electrically integrated into the controller 195. Connections to the leads 186 may be made via a pogo pin, and connections to the leads 187 may be made via the corresponding terminal pins 152 in the electrical connector 150. Although not shown in detail, the integrated test fixture 100 includes leads 186 and 187 and associated voltmeter 185 for each of the junctions 38 of the battery cell interconnect board 10. Overall, the integrated test fixture 100 is configured to apply mechanical stress to each of the junctions 38 of the battery cell interconnect board 10 employing the mechanical stress-inducing device 190 and monitor the electrical connections across the monitored leads 186 and 187 via the controller 195. The mechanical stress may be applied serially or simultaneously to the junctions 38. The controller 195 includes circuits and/or control routines that monitor signals from the voltmeter 185 to evaluate the battery cell interconnect board 10. The controller 195 determines that the battery cell interconnect board 10 has been fabricated in accordance with specifications only when the all of the junctions 38 function in accordance with specification, as indicated by the voltage drops thereacross.

Embodiments in accordance with the present disclosure may be in the form of an apparatus, a method, or a computer program product. Accordingly, the present disclosure may take the form of an entirely hardware embodiment, an entirely software embodiment (including firmware, resident software, micro-code, etc.), or an embodiment combining software and hardware aspects that may all generally be referred to herein as a "module" or "system." Furthermore, the present disclosure may take the form of a computer program product embodied in any tangible medium of expression having computer-usable program code embodied in the medium.

The detailed description and the drawings or figures are supportive and descriptive of the present teachings, but the scope of the present teachings is defined solely by the claims. While some of the best modes and other embodiments for carrying out the present teachings have been described in detail, various alternative designs and embodiments exist for practicing the present teachings defined in the appended claims.

The invention claimed is:

1. A test fixture for evaluating a junction between an electrical lead trace and a busbar, comprising:
    an electric power supply disposed to supply electric power to the electrical lead trace;
    an electric monitoring device disposed to monitor electrical potential across the junction between the electrical lead trace and the busbar; and
    a mechanical stress-inducing device disposed to apply a mechanical stress proximal to the junction;
    wherein the electric monitoring device monitors the electrical potential across the junction of the electrical lead trace coincident with the mechanical stress-inducing device applying mechanical stress proximal to the junction when the electric power supply is supplying electric power to the electrical lead trace; and
    wherein the electric monitoring device determines the electrical integrity of the junction based upon the monitored electrical potential across the junction.

2. The test fixture of claim 1, wherein the mechanical stress-inducing device disposed to apply a mechanical stress proximal to the junction comprises a nozzle of a high-pressure source that is aimed towards the junction.

3. The test fixture of claim 2, wherein the nozzle of the high-pressure source is disposed to apply a burst of pressurized airflow to the junction.

4. The test fixture of claim 1, wherein the mechanical stress-inducing device disposed to apply a mechanical stress proximal to the junction comprises a hammer device that is disposed to tap on the junction.

5. The test fixture of claim 4, wherein the hammer device is disposed to apply a direct mechanical tapping onto the junction.

6. The test fixture of claim 1, wherein the mechanical stress-inducing device disposed to apply a mechanical stress proximal to the junction comprises an ultrasonic welding device including a horn that is placed in contact with the junction.

7. The test fixture of claim 5, wherein the horn of the ultrasonic welding device is disposed to induce vibration at the junction.

8. The test fixture of claim 1, wherein the electric monitoring device is disposed to determine that the junction has been formed in accordance with its specification when the electrical conductivity across the electrical connector and the busbar is greater than a threshold conductivity during the induced mechanical stress.

9. The test fixture of claim 1, wherein the electric monitoring device is disposed to determine that the junction has not been formed in accordance with its specification when the electrical conductivity across the electrical connector and the busbar is less than a threshold conductivity during the induced mechanical stress.

10. A method for evaluating a junction that is formed between an electrical lead trace and a busbar, the method comprising:
    connecting an electrical test fixture disposed to monitor electrical conductivity across the electrical connector and the busbar;
    applying an electrical potential across the electrical connector and the busbar;
    inducing a mechanical stress proximal to the junction and coincidently monitoring the electrical conductivity across the electrical connector and the busbar employing the electrical test circuit; and
    evaluating integrity of the junction based upon the monitoring of the electrical conductivity across the electrical connector and the busbar when inducing the mechanical stress.

11. The method of claim 10, wherein evaluating integrity of the junction comprises determining that the junction has been formed in accordance with its specification when the electrical conductivity across the electrical connector and the busbar is greater than a threshold conductivity when inducing the mechanical stress.

12. The method of claim 10, wherein evaluating integrity of the junction comprises determining that the junction has not been formed in accordance with its specification when the electrical conductivity across the electrical connector and the busbar is less than a threshold conductivity when inducing the mechanical stress.

13. The method of claim 10, wherein applying a mechanical stress proximal to the junction between the electrical lead trace and the busbar comprises applying a burst of pressurized airflow to the junction.

14. The method of claim 10, wherein applying a mechanical stress proximal to the junction between the electrical lead trace and the busbar comprises mechanically tapping onto the junction.

15. The method of claim 10, wherein applying a mechanical stress proximal to the junction between the electrical lead trace and the busbar comprises inducing a mechanical vibration at the junction.

16. A test fixture for evaluating a battery cell interconnect board, wherein the battery cell interconnect board includes a plurality of junctions between a plurality of electrical lead traces and a corresponding plurality of busbars, comprising:
an electric power supply disposed to supply electric power to the plurality of electrical lead traces;
a controller including an electric monitoring device, wherein the controller is disposed to monitor electrical potential across each of the junctions between the electrical lead traces and the busbars; and
a mechanical stress-inducing device disposed to apply mechanical stress proximal to each of the junctions;
wherein the controller is disposed to control the mechanical stress-inducing device to apply mechanical stress proximal to the junctions when the electric power supply is supplying electric power to the electrical lead trace; and
wherein the controller is disposed to monitor, via the electric monitoring device, the electrical potentials across the junctions of the electrical lead traces.

17. The test fixture of claim 16, wherein the controller is disposed to control the mechanical stress-inducing device to sequentially apply mechanical stress proximal to the junctions.

18. The test fixture of claim 16, wherein the controller is disposed to control the mechanical stress-inducing device to simultaneously apply mechanical stress proximal to the junctions.

19. The test fixture of claim 16, wherein the mechanical stress-inducing device disposed to apply a mechanical stress proximal to the junction comprises a nozzle of a high-pressure source that is aimed towards the junction, wherein the nozzle of the high-pressure source is disposed to apply a burst of pressurized airflow to the junction.

20. The test fixture of claim 16, wherein the mechanical stress-inducing device disposed to apply a mechanical stress proximal to the junction comprises a hammer device that is disposed to tap on the junction, wherein the hammer device is disposed to apply a direct mechanical tapping onto the junction.

* * * * *